US012642823B2

(12) United States Patent
Park et al.

(10) Patent No.: US 12,642,823 B2
(45) Date of Patent: Jun. 2, 2026

(54) SLEEP IMPROVEMENT METHOD USING *LIMOSILACTOBACILLUS REUTERI* STRAIN LM1063

(71) Applicants:LACTOMASON CO., LTD., Jinju-si (KR); KOREA RESEARCH INSTITUTE OF BIOSCIENCE AND BIOTECHNOLOGY, Daejeon (KR)

(72) Inventors: Eun Ju Park, Changwon-si (KR); Yun Jung Lee, Changwon-si (KR); Hee Soo Jeong, Changwon-si (KR); Minn Sohn, Jinju-si (KR); Hyeon Tak Han, Bucheon-si (KR); So Lim Shin, Anyang-si (KR); Doo-Sang Park, Daejeon (KR)

(73) Assignees: LACTOMASON CO., LTD., Jinju-si (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 19/011,691

(22) Filed: Jan. 7, 2025

(65) Prior Publication Data

US 2025/0144158 A1 May 8, 2025

Related U.S. Application Data

(63) Continuation of application No. PCT/KR2024/000141, filed on Jan. 3, 2024.

(30) Foreign Application Priority Data

Mar. 17, 2023 (KR) ........................ 10-2023-0035300

(51) Int. Cl.
*A61K 35/741* (2015.01)
*A23L 33/135* (2016.01)
*A61P 25/00* (2006.01)

(52) U.S. Cl.
CPC .......... *A61K 35/741* (2013.01); *A23L 33/135* (2016.08); *A61P 25/00* (2018.01)

(58) Field of Classification Search
CPC .. A61K 35/741; A61K 35/747; A61K 35/744; A23L 33/135; A61P 25/00; A61P 25/20
See application file for complete search history.

(56) References Cited

FOREIGN PATENT DOCUMENTS

| CN | 103361290 | B1 | 12/2016 | |
|---|---|---|---|---|
| JP | 6127169 | B2 | 5/2017 | |
| KR | 101973937 | B1 | 4/2019 | |
| KR | 102019296 | B1 | 9/2019 | |
| KR | 1020200071910 | A | 6/2020 | |
| KR | 102149404 | B1 | 8/2020 | |
| KR | 1020220112192 | A | 8/2022 | |
| KR | 102559526 | B1 | 7/2023 | |
| KR | 102578662 | B1 | 9/2023 | |
| KR | 1020170051756 | A | 5/2024 | |
| WO | WO-2022130317 | A1 * | 6/2022 | .............. A61P 25/00 |

OTHER PUBLICATIONS

International Search Report of PCT/KR2024/000141 dated Apr. 11, 2024 with machine translations.

* cited by examiner

*Primary Examiner* — Kade Ariani
(74) *Attorney, Agent, or Firm* — NKL LAW; Jae Youn Kim

(57) ABSTRACT

A method according to the present disclosure improves sleep states, maintains a sound sleep, restores the balance of gut microbiota disrupted by sleep disorders, and supports the management of health including metabolic syndrome. Under the provisions of the Budapest Treaty on the International Recognition of the Deposit of Microorganisms for the Purposes of Patent Procedure, the *Limosilactobacillus reuteri* LM1063 strain was deposited with the international depositary authority: the Korean Collection for Type Cultures on Mar. 23, 2017, under the Accession Number: KCTC 13232BP.

6 Claims, 9 Drawing Sheets

<Sleep-inducing test using pentobarbital>

Laboratory Animals : C57BL/6 male (n=8)

Pentobarbital (45mg/kr. i.p.)

| period of adaptation | period of administration | period of fasting | period of test |
|---|---|---|---|
| one week | two weeks
1x10⁹CFU/100 μL
1 time/1 day | one day | 4 hours(10am~2pm) |

Decrease in sleep latency of rodent to which sleep is induced by pentobarbital

Increase in sleep duration of rodent to which sleep is induced by pentobarbital

Induction of sleep by sub-hypnotic dosage of pentobarbital (decrease in sleep latency and increase in sleep duration)

FIG. 1

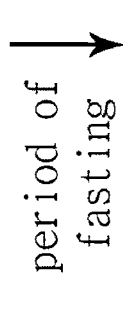
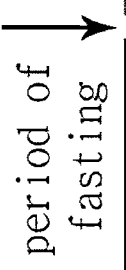

<Sleep-inducing test using pentobarbital>

Laboratory Animals : C57BL/6 male (n=8)

Pentobarbital (30mg/kr. i.p.)

| period of adaptation | period of administration | period of fasting | period of test |
| --- | --- | --- | --- |
| one week | two weeks $1 \times 10^9$CFU/100 μL 1 time/1 day | one day | 4 hours(10am~2pm) |

Induction of sleep by sub-hypnotic dosage of pentobarbital (decrease in sleep latency and increase in sleep duration)

FIG. 2

SLEEP IMPROVEMENT METHOD USING *LIMOSILACTOBACILLUS REUTERI* STRAIN LM1063

TECHNICAL FIELD

The present disclosure relates to a sleep improvement method using *Limosilactobacillus reuteri* strain LM1063.

BACKGROUND

Recently, various studies have increasingly shown that there is bidirectional communication between the gut and the brain, and studies are being conducted on the activities of gut microbiota, responses of the autonomic nervous system connected to the gut, and the regulation of brain function by metabolites or neurotransmitters produced by gut microbiota through the internal communication pathway known as the Microbiota-Gut-Brain Axis. Also, studies are being actively conducted to prevent, treat and alleviate various emotional illnesses, such as depression, Alzheimer's disease, and sleep disorders, by using gut microbiota. In this regard, patent applications relating to association of probiotics with sleep improvement are being filed, such as Korean Patent No. 10-2149404, which provides a composition for preventing, improving or treating sleep disorders comprising fermentation broth of *Bacillus subtilis* and vitamin $B_6$ as effectives ingredients, and Japanese Patent No. 6127169, which provides a sleep-improving agent containing lactic acid bacteria including *Lactobacillus helveticus* MIKI-020, fermented products of the lactic acid bacteria, and bacterial cell disrupted products of the lactic acid bacteria.

Representative examples of the neurotransmitters produced by gut microbiota include acetylcholine and GABA produced by *Limosilactobacillus* species, serotonin and dopamine produced by *Escherichia coli* species, and serotonin produced by *Streptococcus* and *Enterococcus* species.

Clinical studies (with people suffering from jet lag) and animal studies (with mice models with disrupted 24-hour cycles) have reported that gut microbiota imbalance induced by sleep deprivation leads to increased inflammation, weight gain, and elevated blood sugar levels and thus causes diseases, such as obesity, diabetes, and metabolic syndrome.

Therefore, a sleep-improving agent using probiotics and gut microbiota, such as *Lactobacillus*, can improve sleep states, restore the balance of gut microbiota disrupted by sleep disorders, and support the management of health including metabolic syndrome. Accordingly, various probiotic-based sleep aids are being developed.

An analysis of 14 clinical trials on the improvement of sleep by ingestion of probiotics or heat-treated *Lactobacillus* revealed that the ingestion of probiotics or heat-treated *Lactobacillus* for over eight weeks led to a significant improvement in the Pittsburgh Sleep Quality Index (PSQI).

Various precursors of neurotransmitters produced by gut microbiota cross the blood-brain barrier (BBB) and are converted into neurotransmitters, and thus can help improve the brain function for sleep health and play an important role in forming neural networks.

Results of studies on the effects of probiotics on "gut health-sleep health-brain function" have been published. So far, any probiotics for sleep health improvement have not been registered in Korea as individually approved ingredients by the Korean Ministry of Food and Drug Safety.

Therefore, the probiotics for sleep health improvement are expected to have a significant commercial value in the future.

DISCLOSURE OF THE INVENTION

Problems to be Solved by the Invention

The present disclosure is conceived to develop probiotics capable of preventing or treating a sleep disorder which is one of the modern diseases.

However, there may be other problems within the scope understood by a person with ordinary skill in the art.

Means for Solving the Problems

An aspect of the present disclosure provides a method of improving sleep or maintaining a sound sleep, comprising administering an amount of a pharmaceutical composition to a subject in need thereof, wherein the pharmaceutical composition comprises one or more of a *Limosilactobacillus reuteri* strain LM1063 (KCTC13232BP), a culture of the strain, fragments of the strain, and extracts of the strain as an active ingredient.

Another aspect of the present disclosure provides a method of improving sleep or maintaining a sound sleep, comprising administering an amount of a health functional food to a subject in need thereof, wherein the health functional food comprises one or more of a *Limosilactobacillus reuteri* strain LM1063 (KCTC13232BP), a culture of the strain, fragments of the strain, and extracts of the strain as an active ingredient.

Yet another aspect of the present disclosure provides a method of improving sleep or maintaining a sound sleep, comprising administering an amount of a food material to a subject in need thereof, wherein the food material comprises one or more of a *Limosilactobacillus reuteri* strain LM1063 (KCTC13232BP), a culture of the strain, fragments of the strain, and extracts of the strain as an active ingredient.

The food material may include a food composition. Desirably, the food material may be a food material for health functional foods, a functional material for health functional foods, or a food composition for health functional foods, but is not limited thereto.

However, there may be other aspects within the scope understood by a person with ordinary skill in the art.

Effects of the Invention

A composition according to the present disclosure improves sleep states, maintains a sound sleep, restores the balance of gut microbiota disrupted by sleep disorders, and supports the management of health including metabolic syndrome. A strain according to the present disclosure can be used as a main or supplementary ingredient in food products as well as health functional foods along with advancing studies on probiotics.

However, there may be other effects within the scope understood by a person with ordinary skill in the art.

BRIEF DESCRIPTION OF THE DRAWINGS

FIG. 1 is a schematic diagram showing preparation of a sleep-promoted animal model to which sleep is induced by pentobarbital.

FIG. 2 is a schematic diagram showing preparation of an animal model to which sleep is induced by a sub-hypnotic dosage of pentobarbital.

BEST MODE FOR CARRYING OUT THE INVENTION

Figure 3:
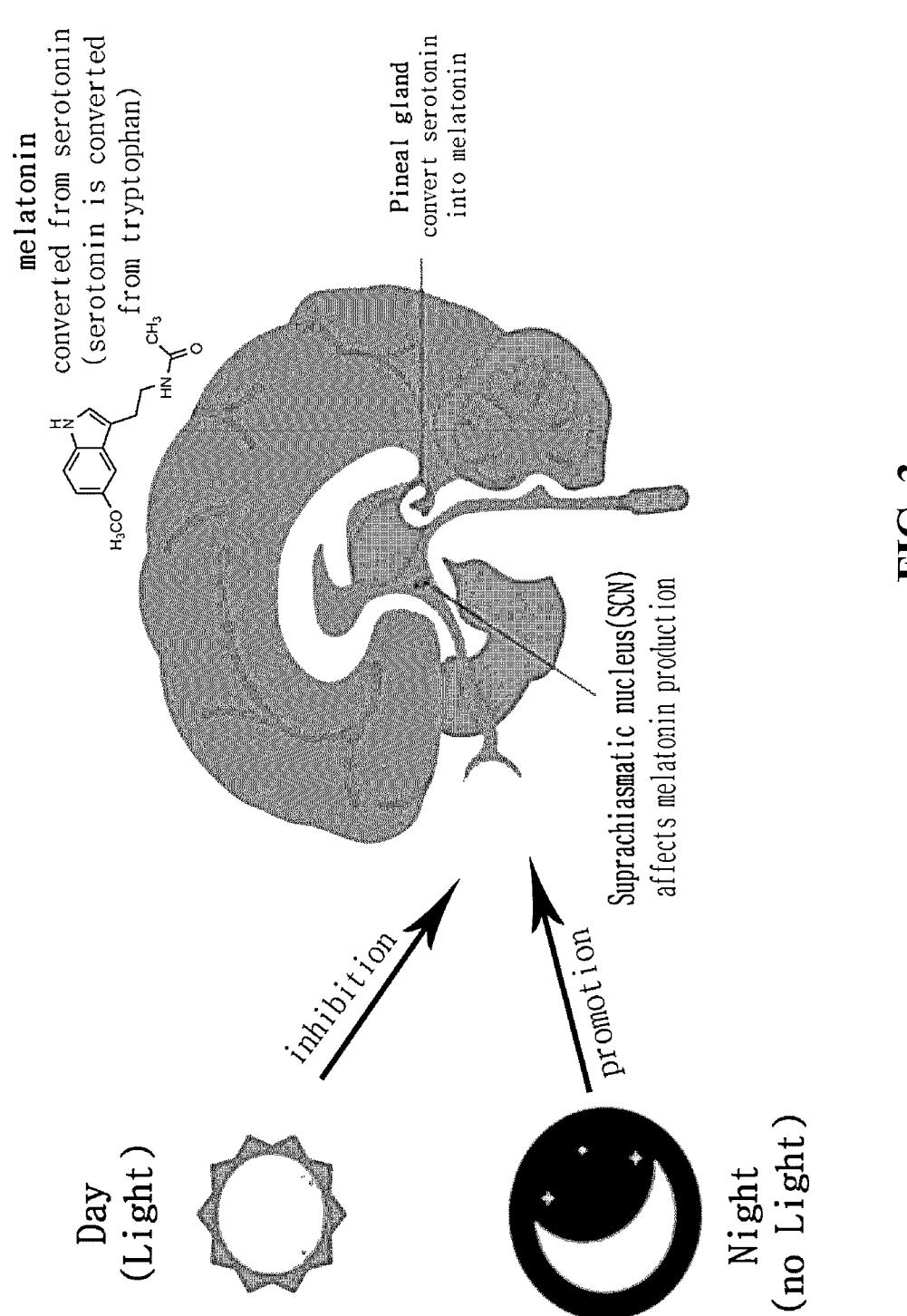
FIG. 3 is a schematic diagram showing production of melatonin depending on the circadian rhythm.

Hereafter, embodiments will be described in detail with reference to the accompanying drawings so that the present disclosure may be readily implemented by a person with ordinary skill in the art. However, it is to be noted that the present disclosure is not limited to the embodiments but can be embodied in various other ways. In the drawings, parts irrelevant to the description are omitted for the simplicity of explanation, and like reference numerals denote like parts throughout the whole document.

Throughout the whole document, the term "comprises or includes" and/or "comprising or including" used in the document means that one or more other components, steps, operation and/or existence or addition of elements are not excluded in addition to the described components, steps, operation and/or elements unless context dictates otherwise.

Throughout the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Under the provisions of the Budapest Treaty on the International Recognition of the Deposit of Microorganisms for the Purposes of Patent Procedure, the *Limosilactobacillus reuteri* LM1063 strain was deposited with the international depositary authority: the Korean Collection for Type Cultures on Mar. 23, 2017, under the Accession Number: KCTC 13232BP.

Throughout the whole document, the term "pentobarbital" refers to (RS)-5-ethyl-5-(1-methylbutyl)-2,4,6(1H,3H,5H)-pyrimidinetrione, and is a substance used for short term sedation, hypnosis, pre-anesthesia, or emergency seizure control. It is also used as an anesthetic by veterinarians.

Throughout the whole document, the term "diazepam" refers to 7-chloro-1-methyl-5-phenyl-3H-1,4-benzodiazepin-2-one, and is a benzodiazepine-based tranquilizer developed by the Swiss company Roche. It is commonly used for treating various diseases including anxiety disorder, alcohol withdrawal syndrome, benzodiazepine withdrawal syndrome, convulsion, seizure, insomnia, and restless legs syndrome and thus classified as a psychotropic drug with potential for misuse and abuse, such as drug dependence.

Throughout the whole document, the term "×g" represents the unit of G-force. G-force is the unit of gravity acceleration and is commonly used to represent a ratio of acceleration generated by centrifugal force during centrifugation.

MODE FOR CARRYING OUT THE INVENTION

Hereafter, embodiments and examples of the present disclosure will be described in detail with reference to the accompanying drawings. However, the present disclosure may not be limited to the following embodiments, examples, and drawings.

1. Test Animal Breeding and Feeding

Test animals, 30 four-week-old male ICR mice, were adapted for one week while being fed with a mouse-specific Lab-chow diet (Harlan, Madison, WI, USA). Based on their body weight, they were divided by a randomized block method into three groups: a control group CON (sleep-induced group), a diazepam group DIZ, and a *Limosilactobacillus reuteri* LM1063 ingestion group S. The mice were fed with an AIN-76 diet as well as a 10% kcal fat diet for three weeks. The composition of the present disclosure was dissolved in distilled water and then administered by a sonde to the normal control group and the diazepam group at a dose of $1\times10^9$ CFU/d once daily. During a breeding duration, a breeding room was maintained at a temperature of $22\pm3°$ C. with a humidity of $55\pm5\%$ under lighting from 07:00 to 19:00 (12-hour cycles).

[Table 1]

Design of improved animal model of sleep health induced by pentobarbital

Group/Pentobarbital/Oral administration (3 weeks)

Control group (Sleep-induced group)/Distilled water

Diazepam group

Ingestion group

\* Administration only when sleep latency and sleep duration are measured

2. Pentobarbital-induced Sleep Test on Sleep-promoted Animal Model

A pentobarbital-induced sleep test using rodents is known as a simple and quick method for evaluating sleep-promoting effects on animals.

As shown in Table 2, the test was conducted to evaluate whether a test substance can further promote sleep induced by pentobarbital, which is an anesthetic. The test substance showed a significant effect in two methods, and was regarded as having sleep-improving function when there was no direct soporific effect.

[Table 2]

Method/Sleep-improving function index

Decrease in sleep latency of rodent to which sleep is induced by pentobarbital

Increase in sleep duration of rodent to which sleep is induced by pentobarbital

Induction of sleep by sub-hypnotic dosage of pentobarbital (decrease in sleep latency and increase in sleep duration)

(1) Sleep-Promoted Animal Model to which Sleep is Induced by Pentobarbital (FIG. 1)

1) Test groups each consisting of ten ICR mice were prepared and the mice were adapted to the laboratory environment for one week. Environmental factors that can affect sleep, such as noise (40 dB or less), lighting (200-300 LUX, 12 hours/day), temperature (22±3° C.), and humidity (55±5%), were controlled during the breeding duration.

2) An effective strain was dissolved in distilled water at a concentration of $1\times10^9$ CFU/100 uL and administered by a sonde daily for two weeks.

3) After fasting for 24 hours prior to the test, a hypnotic dosage of pentobarbital (45 mg/kg) was administered intraperitoneally. A positive control group was administered with diazepam (2 mg/kg) and a negative control group was administered with distilled water.

4) After the treatment with pentobarbital, each animal was transferred to a separate space, and the sleep latency and sleep duration were measured.

5) The sleep latency was defined as the elapsed time from intraperitoneal injection of pentobarbital until the loss of righting reflex for more than one minute, and the sleep duration was defined as the period of time until righting reflex was regained.

(2) Sleep-Promoted Animal Model to which Sleep is Induced by Sub-Hypnotic Dosage of Pentobarbital (FIG. 2)

1) Test groups each consisting of ten ICR mice were prepared and the mice were adapted to the laboratory environment for one week. Environmental factors that can affect sleep, such as noise (40 dB or less), lighting (200-300 LUX, 12 hours/day), temperature (22±3° C.), and humidity (55±5%), were controlled during the breeding duration.

2) An effective strain was dissolved in distilled water at a concentration of $1\times10^9$ CFU/100 uL and administered by a sonde daily for two weeks.

3) After fasting for 24 hours prior to the test, a sub-hypnotic dosage of pentobarbital (30 mg/kg) was administered intraperitoneally. A positive control group was administered with diazepam (2 mg/kg) and a negative control group was administered with distilled water. The test was conducted at a predetermined interval to avoid the effect of the test with a hypnotic dosage of pentobarbital.

4) After the treatment with pentobarbital, each animal was transferred to a separate space, and the sleep latency and sleep duration were measured.

5) The sleep latency was defined as the elapsed time from intraperitoneal injection of pentobarbital until the loss of righting reflex for more than one minute, and the sleep duration was defined as the period of time until righting reflex was regained.

3. Analysis of Melatonin in Blood

It is known that changes in the composition of gut microbiota can increase the level of melatonin in the human body, which improves sleep health. To verify the mechanism of improving sleep health, the level of melatonin needs to be measured.

Blood collected from the test animals was centrifuged at 3000×g for 30 minutes to obtain serum. The obtained serum was used to analyze the relative expression of melatonin in the body at room temperature with a mouse melatonin ELISA kit.

The serum was applied to a plate and reacted at 37° C. for 90 minutes. After the reaction ended, the plate was washed and treated with a biotinylated antibody, followed by a 60-minute reaction at 37° C. After the reaction ended, the plate was washed again and treated with an enzyme conjugate, followed by a 30-minute reaction at 37° C. Then, the reaction was stopped, and the blood melatonin level was measured at 450 nm (FIG. 3).

4. Measurement of GABA in Blood (γ-aminobutyric acid) is an inhibitory neurotransmitter that acts on the central nervous system, and controls neuronal excitation in the nervous system.

GABA binds to receptors to inhibit nerve activity. It is released from presynaptic inhibitory neurons to bind to GABA receptors located on the surface of postsynaptic neurons. The GABA receptors binding to GABA inhibit the excitability of neurons. GABA helps prevent or alleviate stress, tension, anxiety, and panic disorder, and serves as a substance to stabilize sleep activities. Therefore, the effect of improving sleep activities can be confirmed by measuring the levels of GABA in the sleeping animals.

Blood collected from the test animals was centrifuged at 3000×g for 30 minutes to obtain serum. The obtained serum was applied to a washed plate along with a biotin-labeled antibody and reacted at 37° C. for 45 minutes. After the reaction ended, the plate was washed and treated with an HRP-streptavidin conjugate (SABC), followed by a 30-minute incubation at 37° C. Then, the reaction was stopped, and the blood GABA level was measured at 450 nm.

5. Statistical Processing

Statistical processing of all data (Tables 3 through 9) was analyzed using SPSS Statistics 20, and results were expressed as mean±standard error. Statistical significance for mean values was verified at a 95% confidence level ($p<0.05$). Each item was analyzed using one-way analysis of variance (one-way ANOVA) to calculate an F-value, and significance differences among groups were verified by a Duncan's multiple range test. Different superscripts or general characters, such as a, b, c, ab, etc., in each table or drawing indicate that the corresponding values are statistically significantly different from each other. For example, in Table 3, the sleep latency values for the group DIZ and the group S are both marked with "a", which indicates no statistically significant difference, whereas the group CON and the other two groups are marked with different characters, "b" and "a", which indicates a statistically significant difference in the sleep latency. The same applies to Tables 3 through 9.

6. Results

1) Result of Analyzing Effect of Composition of Present Disclosure on Sleep Latency (Time to Fall Asleep) and Sleep Duration in Sleep-Promoted Animal Model to which Sleep is Induced by Pentobarbital The composition of the present disclosure was dissolved and administered orally at a concentration of $1\times10^9$ CFU/100 uL, while a control group was administered with distilled water and diazepam was dissolved and administered orally at a concentration of 2 mg/kg. Within 45 minutes after the administration of the sample, pentobarbital (45 mg/kg) was injected intraperitoneally to analyze the sleep-promoting effect of the composition of the present disclosure.

Each animal was placed into a transparent cage, and the sleep latency defined as the elapsed time from injection of pentobarbital until the onset of onset and the sleep duration defined as the period of time from sleep onset to waking were measured and recorded in seconds.

The sleep latency was defined as the elapsed time from intraperitoneal injection of pentobarbital until the loss of righting reflex for more than one minute, and the sleep duration was defined as the period of time until righting reflex was regained.

The sleep latency decreased and the sleep duration increased in the sleep test group compared to the control group, which confirms that the composition of the present disclosure has a sleep-promoting effect. Also, the sleep latency decreased and the sleep duration increased in the test group to the same extent as in the drug-treated control group, which confirms that the sleep-promoting effect of the composition of the present disclosure is very high.

The group S showed a significant 25.0% decrease in the sleep latency compared to the group CON, and the sleep latency decreased in the group S to the same extent as in the group DIZ.

Figure 4:
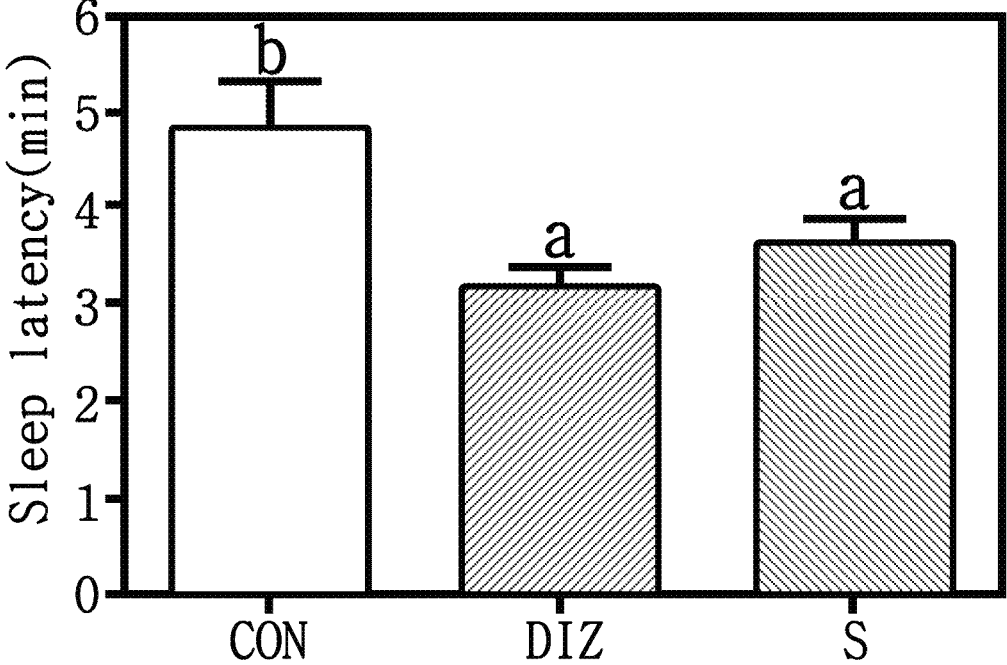
FIG. 4 shows the sleep latency of three groups of animal models to which sleep is induced by pentobarbital.

The above-described results confirmed that the composition of the present disclosure was effective in decreasing the sleep latency (Table 3, FIG. 4).

[Table 3]

Figure 5:
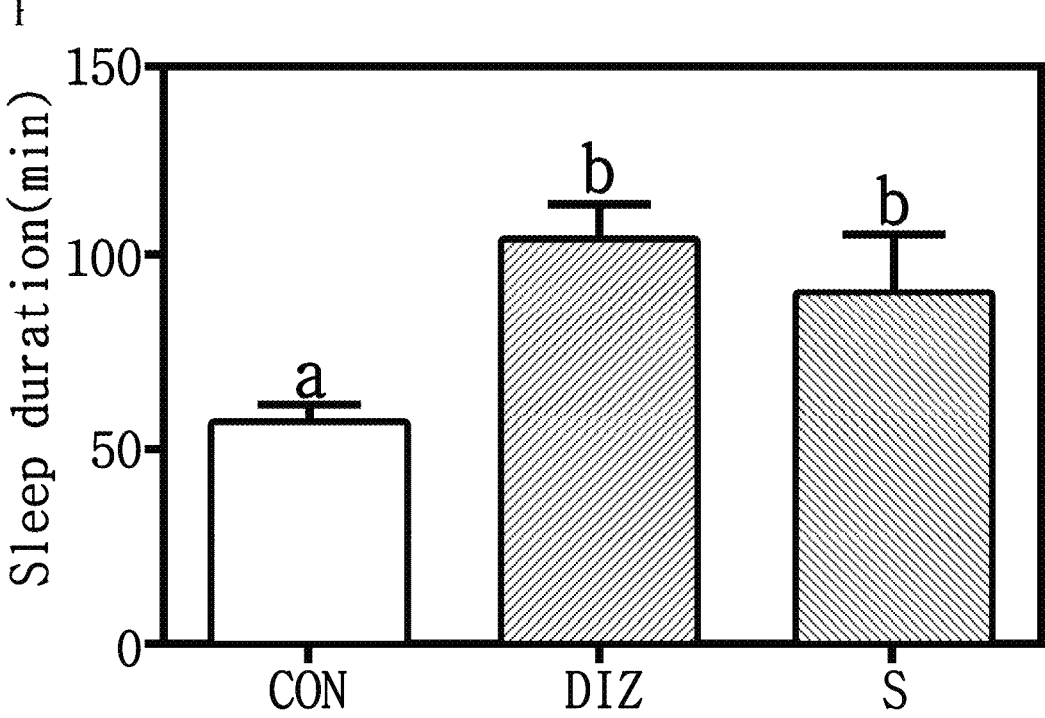
FIG. 5 shows the sleep duration of the three groups of animal models to which sleep is induced by pentobarbital.

Effect of ingestion of composition of present disclosure on sleep latency induced by pentobarbital (unit: min)
Group/Control group (Sleep-induced group)/Diazepam group/Ingestion group For sleep duration, the group DIZ showed a significant increase in the sleep duration compared to the group CON, and the group S also exhibited a significant increase in the sleep duration compared to the group CON with a high effect comparable to that of the group DIZ. Furthermore, the group S demonstrated a sleep-promoting effect by which the group S showed a 60.0% increase in the sleep duration compared to the group CON (Table 4, FIG. 5).

[Table 4]

Effect of ingestion of composition of present disclosure on sleep duration induced by pentobarbital (unit: min)
Group/Control group (Sleep-induced group)/Diazepam group/Ingestion group The above-described results confirmed that the group S affected a decrease in the sleep latency and an increase in the sleep duration in the sleep-promoted animal model administered with 45 mg/kg of pentobarbital, and, thus, the composition of the present disclosure was effective in improving sleep health.

2) Result of Analyzing Effect of Ingestion of Composition of Present Disclosure on Sleep Latency (Time to Fall Asleep) and Sleep Duration in Sleep-Promoted Animal Model to which Sleep is Induced by Sub-Hypnotic Dosage of Pentobarbital The composition of the present disclosure was dissolved and administered orally at a concentration of $1 \times 10^9$ CFU/100 uL, while a control group was administered with distilled water and diazepam was dissolved and administered orally at a concentration of 2 mg/kg. Within 45 minutes after the administration of the sample, a sub-hypnotic dosage of pentobarbital (30 mg/kg) was injected intraperitoneally to analyze the sleep-promoting effect of the composition of the present disclosure.

The sleep latency of the group CON administered with a sub-hypnotic dosage of pentobarbital (30 mg/kg) (16.8±3.2 minutes) was about 12 minutes longer (3.5 times) than that of the group administered with 45 mg/kg of pentobarbital (4.8±0.5 minutes), and the sleep latency of the group DIZ administered with diazepam increased from 3.2±0.2 minutes to 6.0±0.7 minutes (Table 3, Table 5).

The group S exhibited a significant decrease in the sleep latency compared to the group CON with a high effect comparable to that of the group DIZ (Table 5).

Figure 6:
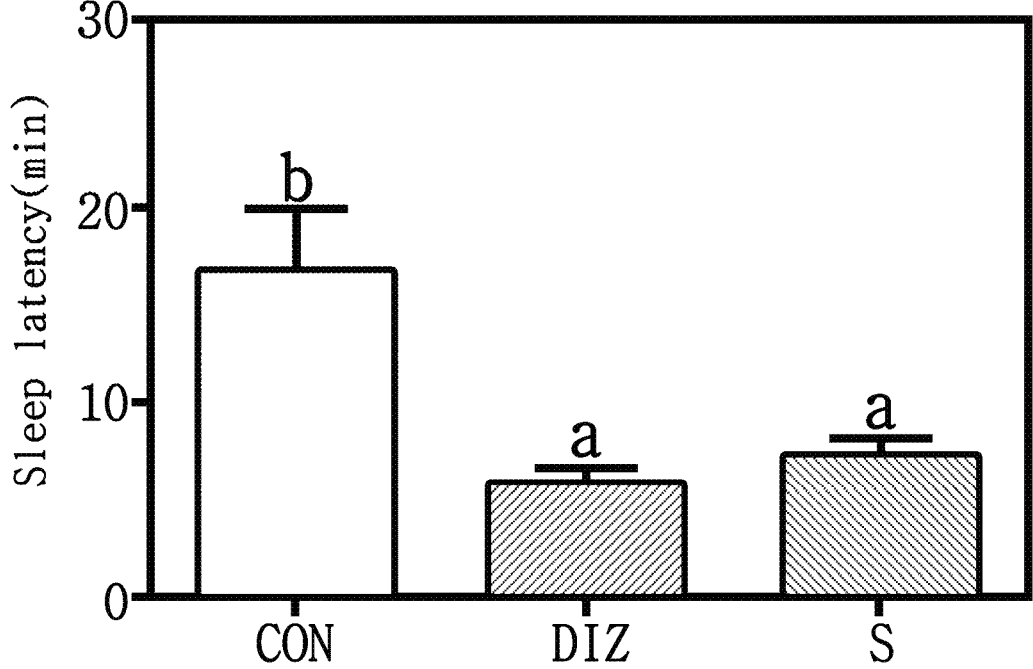
FIG. 6 shows the sleep latency of three groups of animal models to which sleep is induced by a sub-hypnotic dosage of pentobarbital.

The group S demonstrated a sleep-promoting effect by which the group S showed a 56.0% decrease in the sleep latency compared to the group CON (Table 5, FIG. 6).

[Table 5]

Effect of ingestion of composition of present disclosure on sleep latency induced by sub-hypnotic dosage of pentobarbital (unit: min)
Group/Control group (Sleep-induced group)/Diazepam group/Ingestion group The sleep duration of the group CON administered with a sub-hypnotic dosage of pentobarbital (30 mg/kg) (22.1±4.4 minutes) was about 35.4 minutes shorter than that of the group administered with 45 mg/kg of pentobarbital (57.5±4.7 minutes), and the sleep duration of the group DIZ administered with diazepam decreased from 104.4±10.1 minutes to 82.4±7.7 minutes (Table 4, Table 6).

Figure 7:
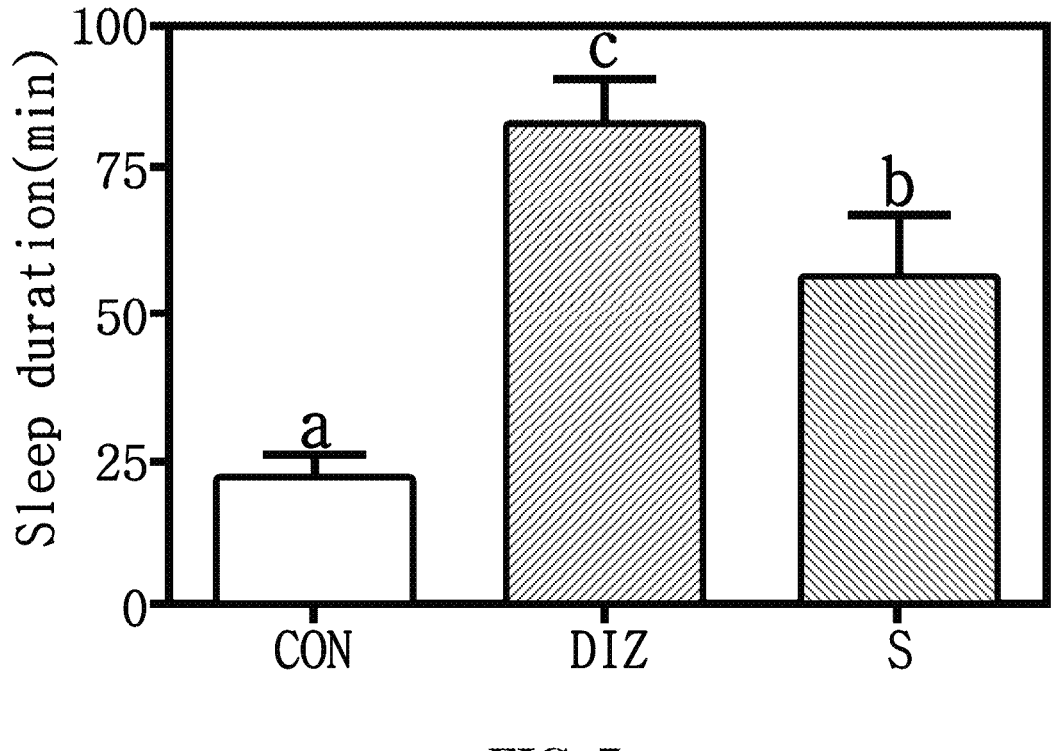
FIG. 7 shows the sleep duration of the three groups of animal models to which sleep is induced by a sub-hypnotic dosage of pentobarbital.

The group S demonstrated a sleep-promoting effect by which the group S showed a 154.8% increase in the sleep duration compared to the group CON (Table 6, FIG. 7).

[Table 6]

Effect of ingestion of composition of present disclosure on sleep duration induced by sub-hypnotic dosage of pentobarbital (unit: min)
Group/Normal control group/Diazepam group/Ingestion group The above-described results confirmed that the group S affected a decrease in the sleep latency and an increase in the sleep duration in the sleep-promoted animal model administered with a sub-hypnotic dosage of pentobarbital (30 mg/kg), and, thus, the composition of the present disclosure was effective in improving sleep health.

Also, the sleep-promoting effect of the composition of the present disclosure was higher when administered with 30 mg/kg of pentobarbital than when administered with 45 mg/kg of pentobarbital. Thus, the composition of the present disclosure is expected to have a high functional potential for improving sleep health.

3) Result of Analyzing Effect of Ingestion of Composition of Present Disclosure on Blood Melatonin Level It is known that changes in the composition of gut microbiota can increase the level of melatonin in the human body, which improves sleep health. To verify the mechanism of improving sleep health, the level of melatonin needs to be measured.

Melatonin, which is involved in the 24-hour circadian rhythm, regulates secretion and physiological functions, and serves as a hormone that relaxes the body and induces sleep. An increase in blood melatonin level can affect promotion of sleep.

Figure 8:
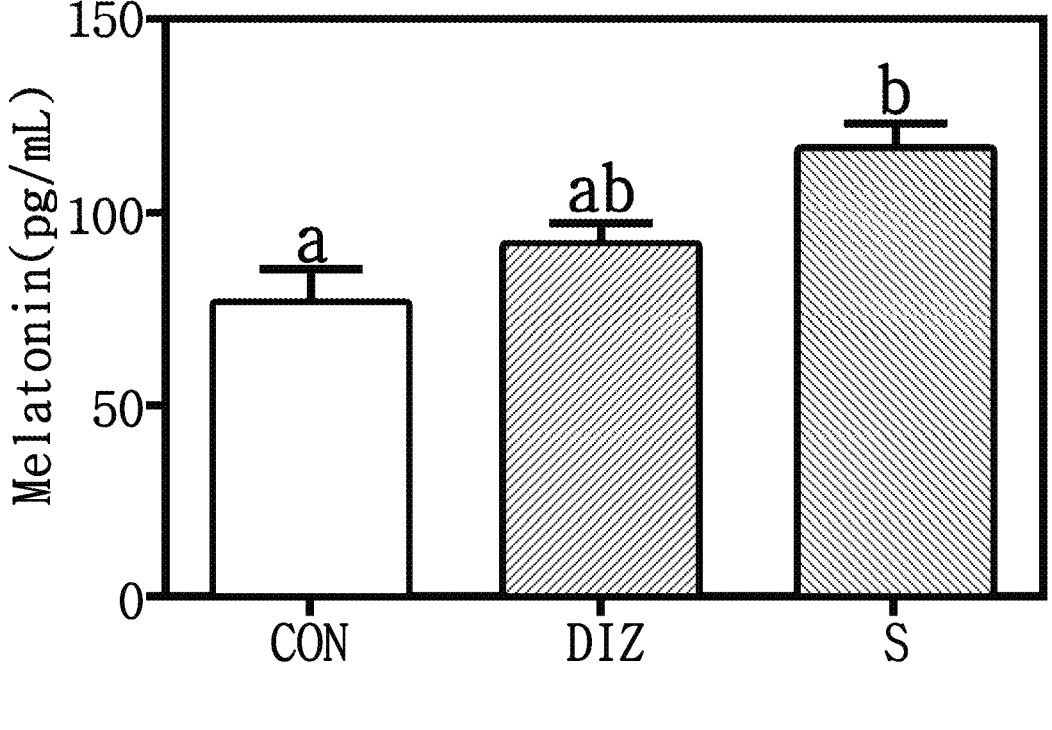
FIG. 8 compares the blood melatonin levels of the three groups of animal models to which sleep is induced by pentobarbital.

After the administration of the composition of the present disclosure, the blood melatonin levels of the group S were significantly higher by 49.8% that those of the group CON (Table 7, FIG. 8).

[Table 7]

Effect of ingestion of composition of present disclosure on blood melatonin level
Group/Control group (Sleep-induced group)/Diazepam group/Ingestion group The above-described results confirmed that the composition of the present disclosure was effective in decreasing the sleep latency and increasing the sleep duration by increasing the blood melatonin level.

4) Result of Analyzing Effect of Ingestion of Composition of Present Disclosure on Blood GABA Level GABA binds to receptors to inhibit nerve activity. It is released from presynaptic inhibitory neurons to bind to GABA receptors located on the surface of postsynaptic neurons. The GABA receptors binding to GABA inhibit the excitability of neurons. An increase in GABA secretion can help stabilize sleep activities.

Figure 9:
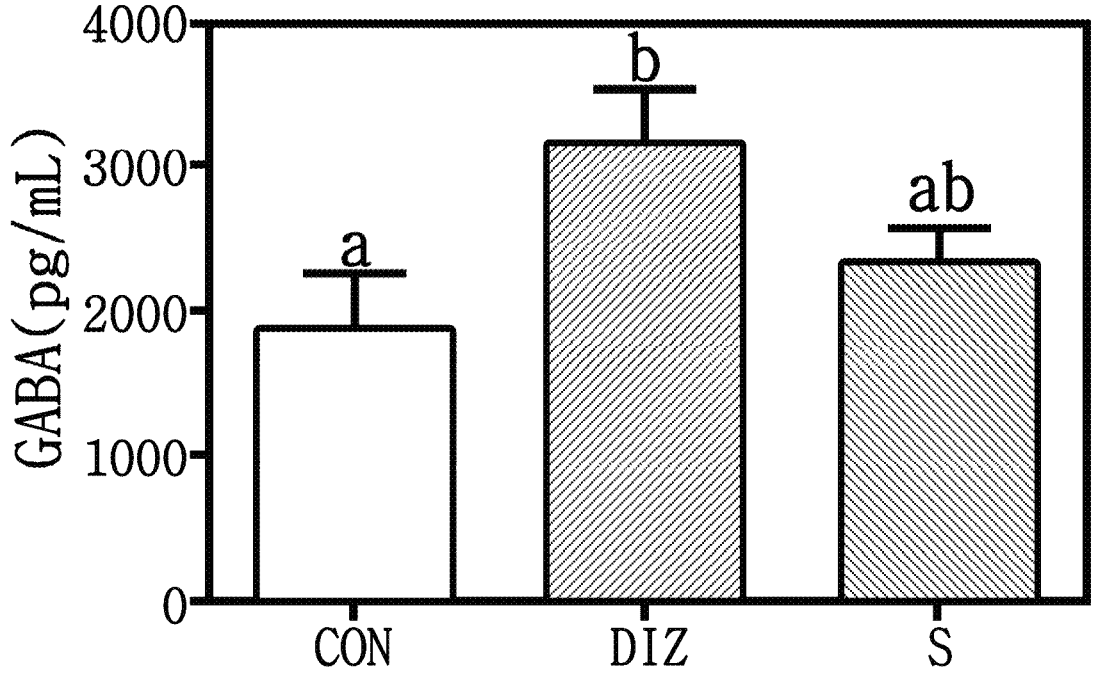
FIG. 9 compares the blood GABA levels of the three groups of animal models to which sleep is induced by pentobarbital.

The group DIZ showed a significant increase in the blood GABA level compared to the group CON, and the group S had blood GABA levels 25.5% higher than the group CON (Table 8, FIG. 9).

The above-described results confirmed that the composition of the present disclosure was effective in improving sleep by increasing the blood GABA level.

[Table 8]

Effect of ingestion of composition of present disclosure on blood GABA level

Group/Control group (Sleep-induced group)/Diazepam group/Ingestion group

We claim:

1. A method of improving sleep, comprising administering an amount of a pharmaceutical composition to a subject in need thereof, wherein the pharmaceutical composition comprises a *Limosilactobacillus reuteri* strain LM1063 deposited under the accession number KCTC13232BP as an active ingredient.

2. The method of claim 1,
   wherein the improving of sleep includes a decrease in sleep latency or an increase in sleep duration.

3. The method of claim 1,
   wherein the composition increases production of melatonin.

4. The method of claim 1,
   wherein the composition increases production of GABA (γ-aminobutyric acid).

5. A method of improving sleep, comprising administering an amount of a health functional food to a subject in need thereof, wherein the health functional food comprises a *Limosilactobacillus reuteri* strain LM1063 deposited under the accession number KCTC13232BP as an active ingredient.

6. A method of improving sleep, comprising administering an amount of a food material to a subject in need thereof, wherein the food material comprises a *Limosilactobacillus reuteri* strain LM1063 deposited under the accession number KCTC13232BP as an active ingredient.

* * * * *